United States Patent [19]

Lauchenauer

[11] Patent Number: 4,491,479

[45] Date of Patent: Jan. 1, 1985

[54] SHAPED SEMI-SOLID ARTICLES

[76] Inventor: Alfred E. Lauchenauer, Bogenstrasse, CH-9326 Horn, Switzerland

[21] Appl. No.: 550,760

[22] Filed: Nov. 10, 1983

[30] Foreign Application Priority Data

Nov. 12, 1982 [GB] United Kingdom ............... 8232394

[51] Int. Cl.$^3$ .................... C09D 5/14; C08L 1/08; A61L 15/00
[52] U.S. Cl. ................... 106/15.05; 106/189; 106/208; 128/156
[58] Field of Search ............ 106/126, 128, 189, 208, 106/213, 15.05; 523/102; 252/522 A, 522 R; 128/156

[56] References Cited

U.S. PATENT DOCUMENTS 3,398,007  8/1968  Pillerdorf et al. .................. 106/128
4,128,507 12/1978  Mitzner ........................... 252/522 A Primary Examiner—Theodore Morris

[57] ABSTRACT

The invention relates to the formation of a semi-solid article by providing a mixture of monomeric aliphatic or aliphatic polyhydroxy compound and the polymeric polyhydroxy compound which is insoluble in the polyhydroxy compound at room temperature, but is soluble therein at elevated temperatures, forming shaped article from said mixture, heating the shaped article so formed so that the polymeric polyhydroxy compound dissolves in a monomeric polyhydroxy compound and cooling the shaped article while maintaining the shape thereof. This produces a semi-solid material which behaves like a solid in the sense that it retains its shape in the absence of chemical stress and resists deformation if mechanical stress is applied and exhibits elasticity if deformed and is restored in a substantial degree to its original shape if mechanical stress causing the deformation is released. It has been found that these semi-solid articles so formed are hydrophilic in that the material is capable of absorbing water or aqueous solution in substantial amounts. The invention also includes slow release device incorporating the semi-solid article produced by the method of the invention.

20 Claims, No Drawings

SHAPED SEMI-SOLID ARTICLES

DESCRIPTION

The present invention relates to semi-solid shaped articles and to a method for producing them. The present invention has particular reference to the production of hydrophilic semi-solid and translucent shaped articles stable at temperatures greater than 100° C.

According to the present invention, there is provided a method of forming a semi-solid shaped article which method comprises
(a) forming a mixture comprising
  (i) a monomeric alicyclic or aliphatic polyhydroxy compound having a ratio between hydroxy groups and carbon atoms of at least 1:4, with
  (ii) a polymeric polyhydroxy compound with is insoluble in said monomeric polyhydroxy compound at room temperature, but is soluble therein at elevated temperatures;
(b) forming a shaped article from said mixture
(c) heating the shaped article so formed to a temperature at which the polymeric polyhydroxy compound dissolves in a monomeric polyhydroxy compound, and
(d) cooling the shaped article while maintaining the shape thereof.

In one embodiment of the invention, the polymeric polyhydroxy compound is present in relation to the monomeric polyhydroxy compound in the ratio 0.5:99.5 to 20:80 by weight.

In a preferred embodiment of the present invention the monomeric compound is an aliphatic compound. The ratio between the hydroxy groups and the carbon atoms in the monomeric compound may be at least 1:3.

For the purposes of the present specification the term "hydrophilic" means that the material is capable of absorbing water or aqueous solutions in substantial amount such as 5 to 50% on the weight of the article. "Semi-solid" means that the material behaves like a solid in the sense that it retains its shape in the absence of mechanical stress, resists deformation if mechanical stress is applied and exhibits elasticity if deformed and is restored in a substantial degree to its original shape if the mechanical stress causing the deformation ceases. As opposed to truly solid bodies, it is more or less elastically deformable within a much higher range of dimensional changes than a rigid solid body.

The term "translucent material" means a material having a thickness of 5 mm which permits a substantial part i.e. greater than 50% of light incidental on one surface to pass through the material. The term "translucent" is intended for the purposes of this specification to include transparent.

"Shaped article" means that the material may be cast, shaped or moulded to have a predetermined shape or form.

The term "substantially non-aqueous" means that the material after forming contains only small amounts (less than 5% by weight) of water.

The products of the invention are substantially hydrophilic, semi-solid and translucent and are stable to temperatures higher than 100° C. The material after shaping does not undergo irreversible changes and may, for example, be exposed to temperatures in the range of 100° to 150° C. for at least 10 minutes without substantial deformation. The material is hydrophilic and will absorb water if exposed to water vapour or liquid. The material after shaping is non-thermoplastic in the sense that it will not melt or become liquid by other reversible mechanisms when exposed to heat.

The monomeric polyhydroxy compounds used in the method of the invention may for example, be glycols such as ethylene glycol, propane-1.3-diol, butane-1.3-diol, glycerol or any other di- or polyhydroxy compound satisfying the hydroxy group/carbon atom requirements specified above. Glycerol, ethylene glycol and propane and butane diols are advantageous from an economic point of view and aliphatic polyols are in general more suitable than alicyclic polyols.

For the purposes of this specification, monomeric polyhydroxy compounds include compounds having a molecular weight which is low relative to that of the polymeric polyhydroxy compounds with which they are combined. They are preferably truly monomeric, but in certain cases a very low polymer having a maximum of five units may be used. Polyhydroxy compounds containing other atoms such, for example, as triethanolamine may be employed.

The polymeric polyhydroxy compound may be selected from polymers containing a ratio of at least one hydroxy group per aliphatic carbon or per carbon atom present in a ring-like structure such for example, as the ring-like structure present in polysaccharides and polyuronides; typical compounds are guar, pectine and derivatives thereof such as esters, hydroxyethyl, methyl ethers and carboxymethylated derivatives and cellulose derivatives. It is preferred, however, that any substituents should not contain groups capable of undergoing secondary reactions with other compounds used in the method.

The mixture may be shaped by casting, or moulding to a predetermined shape or may be calendered or otherwise formed into a sheet-like material.

At room temperature, the shaped mixture comprises two components that are essentially immiscible that is to say, they are not soluble one within the other. During heating it may be desirable to stir the mixture if this does not interfere with the shape of the article or otherwise agitate the same it being desirable that areas prevented from being drawn into the system. Where a cellulose shaped article is desirable, then air or other gas is stirred into the mixture either during or prior to heating and shaping or may be bubbled into the mixture in a known manner. Where positive mixing is carried out, it is preferably carried out at a slightly elevated temperature to reduce the viscosity of the monomeric component. The positive heating step after forming the shaped article should be conducted at a temperature within the range of 100° C. to 170° C., typically 110° C. to 150° C. and preferably 120° C. to 145° C. It will be observed that swelling of the polymeric polyhydroxy compound may start as low as 30° to 40° C. The mixture used to form the shaped article may include components and additives hereinafter described. The components and additives used, however, should be essentially free of water to prevent uncontrollable evaporation of water during heating. As stated above, where shaping is facilitated by a viscosity higher than one of the mixture preheating of the mix to obtain the desired viscosity may be conducted.

The cooling step may be effected simply by causing or allowing the formed shape to cool down and thereafter removing it from a mould. In an alternative embodiment of the invention, the shaped material may be cooled in a water bath prior to removal from the mould.

The invention has the advantage that by varying the ratio between the polyhydroxy compound and the polymeric polyhydroxy compound, the properties of the resultant semi-solid body may be varied over a fairly wide range particularly having regard to its properties of resiliency, hardness, elasticity and tackiness. Furthermore, by varying the compounds, i.e. using, for example, a mixture of polymeric polyhydroxy compounds in different ratios within the parameters defined for the overall mixture other properties such as hydrophilic properties may be varied.

The invention includes the incorporation of additives to the mixture. Such additives being capable, of course, of withstanding the temperatures needed to effect solution, after the shaping step; typical additives are: hydrophobic agents, hydrophilic agents, surfactants, medicaments, pigments, dyestuffs. The resultant semi-solid body is extremely hydrophilic per se; it may be made more resistant to water diffusion and absorption by the addition of hydrophobic agents. It will absorb liquids in contact with it and it may also slowly release agents through diffusion.

It will be appreciated, therefore, that the semi-solid shaped articles in accordance with the present invention and when made by the method of the invention, may be suitable for use as wound dressings which have the particular advantage that they may be substantially transparent if a proper selection of components forming the semi-solid material is made and that the material of the dressing will absorb a fairly high amount of liquid from the wound. A further advantage of wound dressings formed from the semi-solid material in accordance with the present invention is that where it contains most water, i.e. closest to the newly formed skin, it has a lower co-adhesion that in less swollen areas and it may thus be peeled from the wound without tearing or injuring newly formed skin.

The present invention includes semi-solid shaped articles formed by the method of the present invention.

The semi-solid translucent shaped articles in accordance with the present invention are "duraplastic" in the sense that the mixture of components used to prepare the material undergoes an irreversible change of mechanical and physio-chemical properties during the shape forming process.

If semi-solid shaped articles having a very high degree of swelling in water are required, the polymeric polyhydroxy compound should include swellable substances, such as for instance, hydroxy-ethyl cellulose. Such articles will absorb very high percentages of water before they gradually loose their mechanical integrity. They will also absorb ion-containing aqueous solutions such as 0.9% NaCl (physiological common salt solution).

If on the other hand semi-solid shaped articles retaining their mechanical integrity even if they are immersed in water or aqueous solutions, or exposed to water vapour are required, the polymeric polyhydroxy should comprise compounds such as Xanthane in which case the monomeric polyhydroxy compounds may with advantage be a compound such as glycerol. Shaped articles made from such components will swell to a predetermined extent, but will not dissolve or start to flow due to excessive swelling. By using mixtures for instance of hydroxyethyl cellulose and Xanthane and by varying the ratio between monomeric and polymeric polyhydroxy compounds, the degree of swelling may be adjusted to within determined specified limits. While shaped articles showing a slower degree of swelling will take up smaller amounts of aqueous swelling agents, they may still remain permeable to such agents, i.e. they will take up the agent, which will permeate and will release if suitable acceptors for the swelling agent are present.

This not only applies to pure water, but also to aqueous solutions, including salt solutions. Swelling degrees in salt solutions are usually considerably lower than in water alone, i.e. swelling will cause a lower increase of the volume of the shaped article.

Semi-solid shaped articles exhibiting a relatively low degree of swelling may not only be used to absorb aqueous media while retaining the mechanical integrity of their shape over a long time, but they can also serve as slow release systems. Agents to be released may either be added to the components from which the shaped article is formed, or during the formation, or they are made to permeate partly or completely through the formed shaped article before they are brought into contact with the medium to which they have to release the agent. Another method of slow release consists in enclosing or embedding agents to be released into the shaped article, e.g. into vacuities or open space inside the shaped article, an aqueous liquid (into which the article is immersed or with which it is in contact with one or several of its surfaces) serving as vehicle for the agent to carry it at predeterminable diffusion rates out of the shaped article and into the medium to which it is to be released.

Still another application of such shaped articles is to release gradually a vaporisable agent into a gaseous media, the agent per se or in an aqueous solution or as a dispersion may be caused or allowed to permeate the shaped article, or be entrapped within it. When such an article is exposed to the gaseous medium, the agent will be slowly released.

During the formation of semi-solid shaped articles in accordance with the invention, the mixture of the monomeric polyhydroxy compounds and the polymeric polyhydroxy compounds usually has a relatively low viscosity before solution occurs. To facilitate the formation of a shape, it may be advantageous to increase the viscosity by partial solubilisation of the polymeric polyhydroxy component (or a component of a mixture of such compounds) prior to the formation of the shaped body. Such solubilisation may be carried out only to a level where the mixture still shows flow properties under the action of gravity or pressure, total solubilisation and hence transformation into a semi-solid body being effected only after formation of the shape.

As mentioned above, agents to be sorted in, released or leached from shaped semi-solid articles may be added to the mixture of the monomeric and polymeric polyhydroxy compound, during or after partial or complete solubilisation of the polymeric polyhydroxy compound, before or after the formation of a shaped article, into vacuities or open spaces inside the shaped article or it may be made to permeate completely or partly the shaped article after its formation.

Following is a description by way of example only of methods of carrying the invention into effect.

| Examples No. | Polymeric polyhydroxy compound (A) | Polyhydroxy compound (B) | Ratio A:B | Heating Temperature | Cohesion | Transparency | Tackiness |
| --- | --- | --- | --- | --- | --- | --- | --- |
| 1. | Pectin highly esterified | Glycerol | 8:92 | 140° | good | very good | none |
| 2. | same, plus same amount methyl-cellulose | same | 4 + 4:92 | 135° | poor | — | — |
| 3. | Hydroxy-propyl-guar | same | 8:92 | 135° | good | good | fairly high |
| 4. | Hydroxy-ethyl-cellulose | same | 8:92 | 120–1250° | good | none | none |
| 5. | same | same | 8:92 | 135° | very good | very good | light |
| 6. | pectin, highly esterified | same | 8:92 | 140° | poor | good | none |
| 7. | methyl cellulose pectin as above | same | 4:4:92 | 135° | good | good | light |
| 8. | methyl cellulose | same | 10:90 | 135° | very good | good | none |
| 9. | methyl cellulose | propane 1,3 diol | 10:90 | 140° | good | good | medium |
| 10. | same | Butane-1,3 diol | 10:90 | 140° | good | good | very low |
| 11. | same | Butane-1,4 diol | 10:90 | 140° | good | good | none |
| 12. | same | ethylene glycol | 10:90 | 140° | good | good | light |

In each of the Examples 1 to 12, a polymeric polyhydroxy compound (A) was combined in admixture with polymeric polyhydroxy compound (B) in the ratio stated in the accompanying table. The mixture was then shaped in a mould and the shaped material was then heated to the temperature as stated. The properties of the products obtained are set out in the accompanying table.

EXAMPLE 13

To obtain a semi-solid, shaped article with high resistance to loss of mechanical integrity when subjected to swelling, 10% by weight of Xanthane (technical grade) were added to glycerol (substantially water free). No precautions as regards the removal of air bubbles were taken. The mixture was heated to 145° C. for 30 minutes in a mould. After 15 to 20 minutes a semi-solid article formed, which after cooling was removed from the mould.

By the same method, semi-solid shaped articles containing as polymeric polyhydroxy compounds mixtures of hydroxy-ethyl cellulose and xanthane were prepared. Resistance to swelling for these articles was determined by immersion in a 0.9% (by weight) solution of NaCl in water.

The results are listed in the table below:

| Polymeric Polyhydroxy compounds* | % of liquid adsorbed | | Appearance | |
| --- | --- | --- | --- | --- |
| | after 24 h | after 48 h | after 24 h | after 48 h |
| 10% A | ca. 64% | ca. 105% | very low integrity | no integrity |
| 8% A 4% B | 60% | 85% | reduced integr., tacky | very reduced integr. tacky |
| 4% A 8% B | 54% | 63% | slightly reduced integr., tacky | reduced integr., tacky |
| 10% B | 30% | 33% | good cohesion | good cohesion |

*on weight of glycerol
A = hydroxy-ethyl cellulose
B = Xanthane (analytically pure)

The sample with 1% A and 9% B (on weight of glycerol) showed an area increase of about 35% when immersed in 0.9% NaCl solution and of about 100% in pure water, without loosing in either case its mechanical integrity.

The article was used as a transparent wound dressing. The permeability to 0.9% NaCl was 40 g per m²/h.

EXAMPLE 14

A formulation containing 9% of xanthane and one percent of hydroxy-ethyl cellulose (% on weight of glycerol) was prepared by mixing with glycerol, heating the mixture to 145° C. until its viscosity had increased to 8000 centipose and pouring the viscous liquid onto a conveyor belt carrying a release paper, and then completing the formation of a semi-solid shaped article by further heating at 145°–150° C.

EXAMPLE 15

(15a) Semi-solid shaped articles with vacuities were prepared by proceeding as described in Example 3, but stirring air or nitrogen into the liquid whose viscosity was being increased to a level suitable for pouring it onto the shape-forming carrier sheet. Vacuities were formed varying in number and diameter depending on the speed of stirring, the shape of the stirrer head and the way the gaseous medium was introduced into the liquid, and the viscosity level at which gas incorporation into the liquid took place formed.

(15b) A semi-solid shaped article containing vacuities was formed by pouring the viscous pre-heated mixture into a horizontal mould having many protrusions in a pattern, removing the article thus shaped preferably after completing the heating, and laminating the face showing the vacuities to preheated material of the same material, cast in the form of a sheet and completing the heating to achieve mechanical integrity.

EXAMPLE 16

To incorporate a fungicidal agent into a semi-solid shaped article, the following methods were used:
(16a) The fungicidal agent was dissolved in a solvent (hydrocarbon) which was immiscible with glycerol. The first sample was prepared by emulsifying the hydrocarbon containing the fungicidal agent in glycerol, adding the mixture of polymeric polyhydroxylic compounds mentioned in Example (3) and heating as described in the same Example. The boiling point of the hydrocarbon was more than 30° C. higher than the gel-forming temperature.

In the case of the second sample, the hydrocarbon containing the fungicidal agent was stirred into the preheated mixture.

(16b) After preparing two semi-solid shaped articles according to Example (3), the article having a rectangular cross-section (10 cm wide, ½ cm thick, produced in endless form by casting onto conveyor belts), the fungicidal agent was applied to the surface of one of the slabs by a scattering process, whereafter the two slabs were laminated while the surface of the slab not covered with fungicidal agent still was somewhat tacky. The fungicidal was thus trapped between the two slabs.

(16c) The fungicidal agent was applied to the semi-solid shaped article containing voids as described in Example (15b), lamination and thus sealing of the fungicidal agent taking place, only after application of the fungicidal agent into the vacuities.

(16d) The fungicidal agent was first encapsulated in gelatine, and these capsules were stirred into the preheated mixture described in Example (14).

(16e) The fungicidal agent was added to the mixture of the monomeric and the polymeric polyhydroxy compounds
before heating
after preheating In all samples, the fungicidal was gradually released after the semi-solid shaped article had been completely immersed in an aqueous medium, or after it had been completely or partly (locally) permeated by an aqueous medium and left in contact with it at least over some parts or its entire surface, the rate of the diffusion being influenced among other things by the degree of swelling of the article, the initial concentration and location of the fungicidal agent and the presence of internal interfaces around vacuities.

EXAMPLE 17

A bacteriocidal agent was incorporated into semi-solid shaped articles produced by any of the methods described in Example 16.

(17a) The bacteriocidal agent is dissolved in an aqueous liquid having some swelling action on the material of the shaped article. The shaped article was then immersed in this solution until permeation to the desired depth had taken place. With or without previous removal of the solvent, the shaped article slowly started to release the bacteriostatic agent as soon as it was brought into contact with a medium capable causing swelling of the material of the shaped article and acting as a solvent or stray swelling or dispersing agent for the bacteriocidal agent.

This method of application of agents together with the one described in Examples 16b) and 16c) is also suitable for agents which are sensitive to high temperatures, i.e. for agents which might be affected by the temperatures necessary to achieve semi-solid properties of articles consisting of the components described.

The methods described in Examples (16b), (16c) and (17a) may also be used if vapourisable or sublimable agents are to be incorporated into semi-solid shaped articles.

I claim:

1. A method of forming a semi-solid shaped article which method comprises
    (a) forming a mixture comprising
        (i) a monomeric alicyclic or aliphatic polyhydroxy compound having at least one hydroxy group per 4 carbon atoms, with
        (ii) a polymeric polyhydroxy compound which is insoluble in said monomeric polyhydroxy compound at room temperatures, but is soluble therein at elevated temperatures
    (b) forming the shaped article from said mixture
    (c) heated the shaped article to a temperature at which the polymeric polyhydroxy compound dissolves in the monomeric polyhydroxy compound.
    (d) and cooling the shaped article while maintaining the shape thereof
steps (a) and (b) being effected at a temperature insufficient to dissolve the polymeric polyhydroxy compound in the monomeric polyhydroxy compound.

2. A method as claimed in claim 1 characterised in that the polymeric polyhydroxy compound is present in relation to the monomeric polyhydroxy compound in the ratio 0.5:99.5 to 20:80 by weight.

3. A method as claimed in claim 1 or claim 2 wherein the monomeric compound is an aliphatic compound.

4. A method as claimed in claim 1 wherein the monomeric compound has at least 1 hydroxy group for each 3 carbon atoms.

5. A method as claimed in claim 1 wherein the monomeric polyhydroxy compound comprises a polymer containing not more than five recurring units.

6. A method as claimed in claim 1 wherein the monomeric polyhydroxy compound contains atoms other than carbon hydrogen and oxygen.

7. A method as claimed in claim 1 wherein the polymeric polyhydroxy compound contains at least one hydroxy group per aliphatic carbon atom, or per ring-carbon atom.

8. A method as claimed in claim 1 characterised in that the polymeric polyhydroxy compound is capable of absorbing water or an ionic solution.

9. A method as claimed in claim 1 characterized in that at least one agent for subsequent release to the surroundings is incorporated in said mixture or in said shaped article.

10. A method as claimed in claim 1 wherein the monomeric polyhydroxy compound is a glycol.

11. A method as claimed in claim 10 in which the glycol is ethylene glycol, propane diol, or butane diol.

12. A method as claimed in claim 1 in which the monomeric polyhydroxy compound is glycerol.

13. A method as claimed in claim 1 in which the polymeric polyhydroxy compound is selected from the group consisting of guar and ethers or esters thereof, pectine and ethers or esters thereof and cellulose ethers and esters.

14. A method as claimed in claim 1 in which the shaped article is heated in step (c) to a temperature of 100°–170° C.

15. A method as claimed in claim 14 in which said heating is to 110° to 150° C.

16. A method as claimed in claim 15 in which the heating is to 120°–145° C.

17. A method as claimed in claim 14 in which the mixture comprises glycerol, xanthane, and hydroxyethyl cellulose.

18. A method as claimed in claim 14 in which the mixture comprises glycerol and hydroxypropyl guar.

19. A slow release element comprising a semisolid article produced by the method of claim 9.

20. A slow release element as claimed in claim 19 which is hydrophilic and translucent.

* * * * *

UNITED STATES PATENT AND TRADEMARK OFFICE
CERTIFICATE OF CORRECTION

PATENT NO. : 4,491,479
DATED : Jan. 1, 1985
INVENTOR(S) : Alfred E. Lauchenauer

It is certified that error appears in the above—identified patent and that said Letters Patent are hereby corrected as shown below:

In the heading of the patent,
-- [73] Assignee: Adnovum AG
                  Switzerland --

Signed and Sealed this

Second Day of July 1985

[SEAL]

Attest:

DONALD J. QUIGG

Attesting Officer     Acting Commissioner of Patents and Trademarks